US005629210A

United States Patent [19]

Hercules et al.

[11] Patent Number: 5,629,210

[45] Date of Patent: May 13, 1997

[54] RAPID SCREENING TEST FOR SMITH-LEMLI-OPITZ SYNDROME

[75] Inventors: David M. Hercules, Nashville, Tenn.; Edwin W. Naylor, Pittsburgh, Pa.; Paul A. Zimmerman, Beaverton, Oreg.

[73] Assignee: University of Pittsburgh of the Commonwealth System of Higher Education, Pittsburgh, Pa.

[21] Appl. No.: 458,199

[22] Filed: Jun. 2, 1995

[51] Int. Cl.$^6$ .................................................. B01D 59/44
[52] U.S. Cl. .......................... 436/71; 436/173; 436/177; 436/811
[58] Field of Search .............................. 436/71, 173, 63, 436/177, 811

[56] References Cited

U.S. PATENT DOCUMENTS 4,224,031  9/1980  Mee et al. .
5,210,412  5/1993  Levis et al. .

OTHER PUBLICATIONS

94270409 Medline "Abnormal Bile Acids in the Smith--Lemliopitiz Syndrome" (1994 May 1).
Millington et al., "Tandem Mass Spectrometry: A New Method for Acylcarnitine Profiling with Potential for Neonatal Screening for Inborn Errors of Metabolism", *J. Inher. Metab. Dis.*, vol. 13, pp. 321–324, 1990.
Axelson, "Occurrence of isomeric dehydrocholesterols in human plasma", *J. Lipid Res.*, vol. 32, pp. 1441–1448, 1991.
Chace et al., "Rapid Diagnosis of Phenylketonuria by Quantitative Analysis for Phenylalanine and Tyrosine in Neonatal Blood Spots by Tandem Mass Spectrometry", *Clin. Chem.*, vol. 39, pp. 66–71. 1993.
Tint et al., "Defective Cholesterol Biosynthesis Associated with the Smith–Lemli–Opitz Syndrome", *N. Eng. J. Med.*, vol. 330, pp. 107–113, 1994.
Opitz et al., "Cholesterol Metabolism in the RSH/Smith–Lemli–Opitz Syndrome: Summary of an NICHD Conference", *Amer. J. Med. Genet.*, vol. 50, pp. 326–338, 1994.
Opitz et al., "Smith–Lemli–Opitz (RSH) Syndrome Bibliography: 1964–1993", *Amer. J. Med. Genet.*, vol. 50, pp. 339–343, 1994.

*Primary Examiner*—Lyle A. Alexander
*Attorney, Agent, or Firm*—Arnold B. Silverman; Diane R. Meyers; Eckert Seamans Cherin & Mellott

[57] ABSTRACT

A rapid screening test was used to distinguish between blood of normal infants and that of individuals having the Smith-Lemli-Opitz Syndrome (SLO). Blood was spotted on filter paper and analyzed with no extractions or separations. The method comprises the steps of vaporizing a cholesterol containing organic sample, ionizing the vaporized sample, detecting fragment ions of said vaporized ionized sample, and determining the intensity ratio of said fragment ions for cholesterol/7-dehydrocholesterol in the sample. The method includes performing the analysis by time-of-flight secondary ion mass spectrometry without derivation or chemical steps.

9 Claims, 4 Drawing Sheets

RAPID SCREENING TEST FOR SMITH-LEMLI-OPITZ SYNDROME

BACKGROUND OF THE INVENTION

1. Field of the Invention

The present invention relates to the use of Time-of-Flight secondary ion mass spectrometry (TOF-SIMS) for the creation of a diagnostic screening method for Smith-Lemli-Opitz (SLO) Syndrome. The diagnostic allows direct analysis of complex organic matrixes, like blood spots, with 100% accuracy. SLO syndrome is widespread, but the extent of its occurrence is not fully known because of the lack of a suitable screening procedure. The present method provides such a screening procedure.

2. Description of the Prior Art

Neonatal screening has become standard practice in most industrialized nations with virtually every newborn being routinely screened for phenylketonuria (PKU) and congenital hypothyroidism. Both conditions result in severe mental retardation if not diagnosed in the immediate newborn period and started on treatment. Many newborn screening programs have also added tests for additional conditions including sickle cell anemia, galactosemia, maple syrup urine disease, homocystinuria, congenital adrenal hyperplasia, biotinidase deficiency, and cystic fibrosis. The supplemental newborn screening program in place in Pittsburgh, Pa., is unique in that it offers screening for over 35 disorders using a variety of methods including acylcarnitine and amino acid profiling by tandem mass spectrometry for inborn errors of fatty acid, organic acid, and amino acid metabolism (Millington et al., "Tandem mass spectrometry: A new method for acylcarnitine profiling with potential for neonatal screening for inborn errors of metabolism ", *J. Inher. Metab. Dis.*, Vol. 13, pp. 321–324, 1990; Chace et al., "Rapid diagnosis of phenylketonuria by quantitative analysis for phenylalanine and tyrosine in neonatal blood spots by tandem mass spectrometry", *Clin. Chem.*, Vol. 39, pp. 66–71, 1993). Screening is generally carded out on a capillary blood specimen collected by heel stick and spotted on a filter paper card, which in turn can be mailed to a central laboratory for testing.

An interest in testing for the Smith-Lemli-Opitz (SLO) syndrome of newborns has been increasing. Clinically, the SLO syndrome is quite variable, but is generally characterized by microcephaly, growth retardation, mid-face displasia, syndactyly, polydactyly, cataracts, heart and kidney malformations, and mental retardation. Recently, a biochemical marker has been shown to be present in a large majority of SLO patients. This defect in 7-dehydrocholesterol reductase was identified (Tint et al., "Defective cholesterol biosynthesis associated with the Smith-Lemli-Opitz syndrome", *N. Eng. J. Med.*, Vol. 330, pp. 107–113, 1994) and results in a significant reduction in blood cholesterol and a marked increase in its precursor 7-dehydrocholesterol. The frequency of the SLO syndrome has been estimated to be 1 in 20,000 newborns (Opitz et al., "Smith-Lemli-Opitz (RSH) syndrome bibliography: 1964–1993", *Amer. J. Med. Genet.*, Vol. 50, pp. 339–343, 1994).

Techniques such as routine biochemical assays and tandem mass spectrometry have not as yet been successful (Opitz et at., "Cholesterol metabolism in the RSH/Smith-Lemli-Opitz syndrome: Summary of an NICHD conference", *Amer. J. Med. Genet.*, Vol. 50, pp. 326–338, 1994). Currently, the preferred method of diagnosis involves capillary gas chromatography-mass spectrometry of plasma sterols following solvent extraction (Axelson, "Occurrence of isomeric dehydrocholesterols in human plasma", *J. Lipid Res.*, Vol. 32, pp. 1441–1448, 1991). This requires derivation or chemical steps before analysis.

U.S. Pat. No. 4,224,031 by Mee et at. describes a method for analyzing organic materials in blood by chemical ionization mass spectrometry which employs a conventional mass spectrometer. The practice of the method is extraction and derivation, i.e., the use of chemical workup to carry out the analysis. In contrast, the present invention analyzes the blood spots on the filter paper directly without derivation or chemical steps.

U.S. Pat. No. 5,210,412 by Levis et al. utilizes, among other types of mass spectroscopy, a time-of-flight mass analyzer. The key point of the method is derivation of metabolites, proteins or nucleic acids with chromophores that absorb visible radiation. A two laser system is used to induce ionization. The first laser sputters the material into the vacuum and the second laser causes the ionization. In contrast, the invention of the present application utilizes a pulsed ion beam system which both sputters and ionizes the sample.

Therefore, a real and substantial need for a new analytical method that will permit detection of SLO and other additional significant and potentially treatable conditions utilizing the filter paper blood specimen remains.

SUMMARY OF THE INVENTION

Until now, there has been no screening test that could be routinely applied to the specimen. The present invention has met the above-described need. In the method of the present invention, complex organic samples are analyzed for SLO and other inherited metabolic disorders. The steps comprise vaporizing a cholesterol containing organic sample, ionizing the vaporized sample, detecting fragment ions of said vaporized ionized sample and determining a ratio of said fragment ions for cholesterol/7-dehydrocholesterol in said sample. The method includes performing the analysis by using time-of-flight mass spectrometry without derivation or chemical steps. The vaporizing and ionizing steps are performed together by bombardment of the sample with a ca. 10 kiloelectronvolt (KeV) ion beam consisting of, but not limited to, positive argon ions. The method includes employing blood plasma as a sample. The method further includes blood spotted on filter paper as a sample. The method further includes using serum as a sample. The method includes determining a positive test for SLO if the ratio of cholesterol/7-dehydrocholesterol peaks is less than about 3.5. The method also includes determining if the cholesterol to 7-dehydrocholesterol peak ratio is less than 0.5. The method further includes determining that the test for SLO syndrome is negative if the peak ratio of cholesterol/7-dehydrocholesterol is greater than or equal to 10.

It is an object of the present invention to provide a new analytical method that will allow rapid screening for SLO syndrome.

It is an object of the present invention to provide a new analytical method that will permit the detection of additional significant and potentially inherited metabolic disorders or conditions.

It is an object of this invention to offer both sensitivity and high mass resolution which enables unambiguous determination of the analyte with this rapid screening test.

It is an object of this invention that this rapid screening test can be used for analysis of samples which are complex organic matrixes like blood.

It is another object of this invention to eliminate chromatography separation steps in the rapid screening test.

It is another object of this invention to reduce contamination with the rapid screening test.

It is yet another object of this invention to reduce analysis time with the rapid screening test.

It is yet another object of this invention to potentially reduce per-specimen cost.

It is an object of this invention to use TOF-SIMS for the direct analysis of dried filter paper specimens and its use for detection of the SLO syndrome.

The invention will be more fully understood from the following detailed description of the invention.

BRIEF DESCRIPTION OF THE DRAWINGS

A full understanding of the invention can be appreciated from the following detained description of the invention when read with reference to the accompanying graphs.

FIG. 1 discloses a TOF-SIMS spectra of:

a. filter paper blood specimen from a normal individual b. filter paper plasma specimen from a normal individual c. cholesterol standard on filter paper.

FIG. 2 discloses a TOF-SIMS spectra of:

a. filter paper whole blood specimen from a SLO patient b. 7-dehydrocholesterol standard on filter paper.

Figure 3:
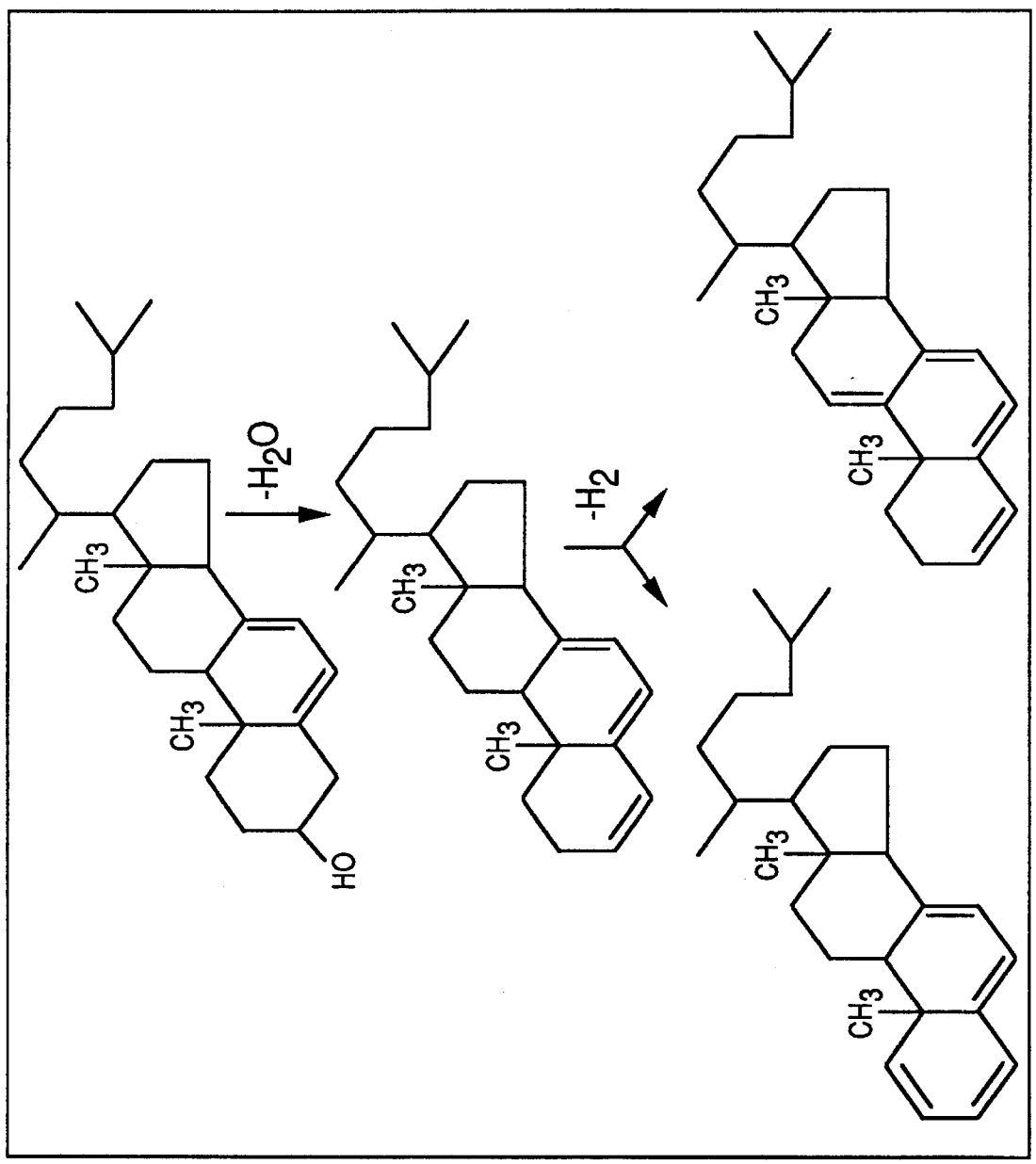

FIG. 3 shows suggested fragmentation for 7-dehydrocholesterol.

FIG. 4 shows TOF-SIMS spectra from unknown sample set:

a. SLO patient b. normal individual.

DESCRIPTION OF THE PREFERRED EMBODIMENTS

The SLO syndrome results in an abnormally low concentration of blood cholesterol and an elevated concentration of 7-dehydrocholesterol. As used herein, the terms "patient" and "newborn" are limited to human beings.

The screening test for the biochemical defect in the SLO syndrome that is presented here can detect an abnormal cholesterol/7-dehydrocholesterol ratio in dried filter paper blood specimens collected from newborns as well as older patients. It meets the criteria for new screening tests set forth by the World Health Organization ("Screening for inborn errors of metabolism", Report of WHO Scientific Group, *WHO Tech. Rep. Ser. No.* 401, Geneva, 1968) and the United States National Academy of Sciences ("Genetic screening. Programs, principles and research", Report of the Committee for the Study of Inborn Errors of Metabolism, Washington, D.C., 1975). It has demonstrated repeatability and accuracy and the sensitivity and specificity of the assay are good. While the initial cost of the equipment is high, the per-specimen cost is low and can be automated. It has also been found that the cholesterol/7-dehydrocholesterol intensity ratio (369.3/365.3) is sufficiently stable to permit reliable newborn screening.

In order for routine newborn screening for an inherited metabolic condition to be acceptable, the seriousness and incidence of the disorder must be sufficiently high; the prognostic diagnosis of individuals identified by screening must be accurate; and there must be some benefit to the patient, his family, and society. With regard to the SLO syndrome, the seriousness of the condition and its relatively high incidence have been well documented. There is optimism that some form of dietary therapy might be effective in some patients with the SLO syndrome. If such therapy is to be effective, it is likely that early diagnosis through newborn screening will be essential.

In general, the present invention contemplates using complex organic samples, like blood, to be analyzed for SLO and other inherited metabolic disorders. The steps comprise vaporizing a cholesterol containing organic sample, ionizing the vaporized sample, detecting fragment ions of said vaporized ionized sample and determining a ratio of said fragment ions for cholesterol/7-dehydrocholesterol in said sample. The method includes performing the analysis by using time-of-flight mass spectrometry without derivation or chemical steps. The vaporizing and ionizing steps are performed together by bombardment of the sample with a ca. 10 kiloelectronvolt (KeV) ion beam consisting of, but not limited to, positive argon ions. The method includes employing blood plasma as a sample. The method further includes blood spotted on filter paper as a sample. The method further includes employing serum as a sample. The method includes determining a positive test for SLO if the ratio of cholesterol/7-dehydrocholesterol peaks is less than about 3.5. The method also includes determining if the cholesterol to 7-dehydrocholesterol peak ratio is less than 0.5. The method further includes determining that the test for SLO syndrome is negative if the peak ratio of cholesterol/7-dehydrocholesterol is greater than or equal to 10.

EXAMPLE

The analyses were performed using an Ion-Tof (Münster, Germany) TOF-SIMS III. This instrument uses a primary ion beam bombarding a surface with 10 keV argon ions to produce secondary organic ions, and has been described in Meyer et al., "Quantification of molecular secondary ion mass spectrometry by internal standards", *Org. Mass Spectrum,* Vol. 27, pp. 1148–1150, 1992. The primary ion beam is pulsed and has a repetition rate of 5 kHz. The primary ion current used for obtaining spectra was about 0.5 pA with a pulse length of 800 ps. Charge compensation was accomplished using a 10 eV electron beam pulsed out of phase with the extraction field and primary ion beam. Spectra were obtained using the ion counting mode with a time-to-digital (TDC) resolution of 472 ps and total time range of 160 µs. Spectra were accumulated for 100 s from an area of approximately 100 µm$^2$.

The filter paper whole blood and plasma specimens were supplied by Magee-Womens Hospital and New Gen Screening, Inc. (Pittsburgh, Pa.), The Kennedy Krieger Institute (Baltimore, Md.) and the New England Regional Newborn Screening Program (Boston, Mass.). The filter paper samples (3.2 mm discs) were introduced directly into the transfer chamber and pumped down to a pressure of about 5×10$^{-6}$ mbar before introduction into the main chamber. The 7-dehydrocholesterol and cholesterol standards were obtained from Sigma Chemical Inc. (St. Louis, Mo.).

TOF-SIMS is a viable technique for screening for the SLO syndrome in newborns. There is a clear difference in spectra obtained from blood spots from normal individuals and those afflicted with the disorder. In fact, the TOF-SIMS results show a good quantitative correlation between the cholesterol/7-dehydrocholesterol intensity ratio (369.3/365.3) and the clinical observations for each patient.

The appropriate TOF-SIMS spectra can be obtained directly from blood specimens spotted on filter paper cards without additional sample preparation. It is also possible to quantitate cholesterol and 7-dehydrocholesterol directly on the filter paper since previous work involving quantitation on paper has yielded reasonable success. Additionally, TOF-SIMS continues to be investigated as a technique for the routine screening of newborns for other inherited metabolic disorders.

Figure 1C:
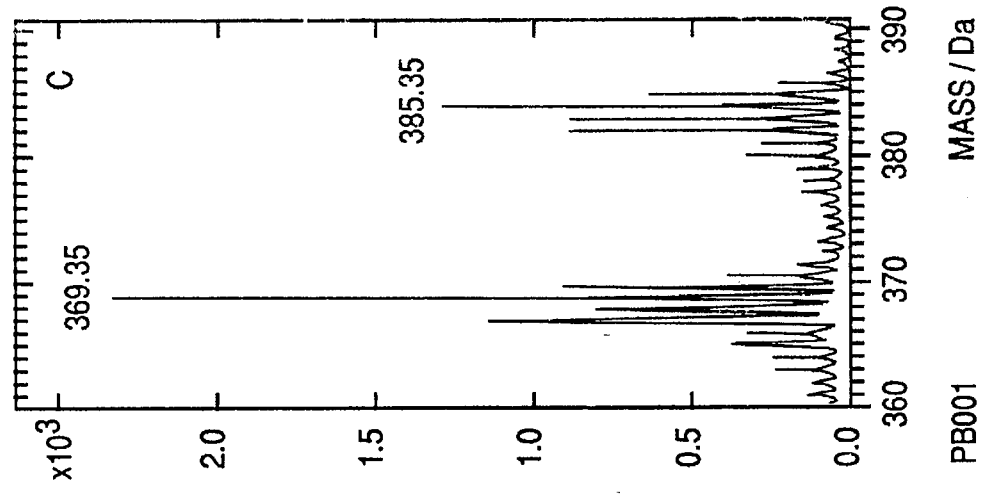
Figure 1B:
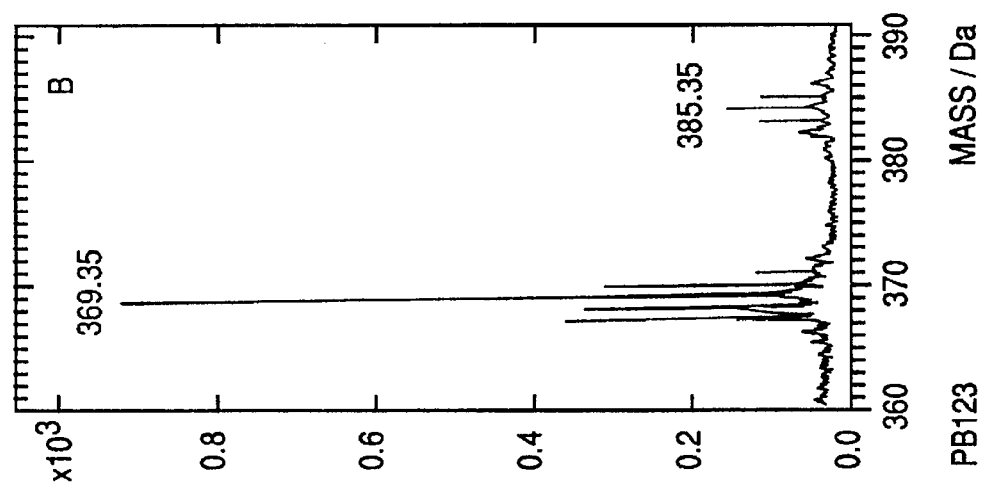
Figure 1A:
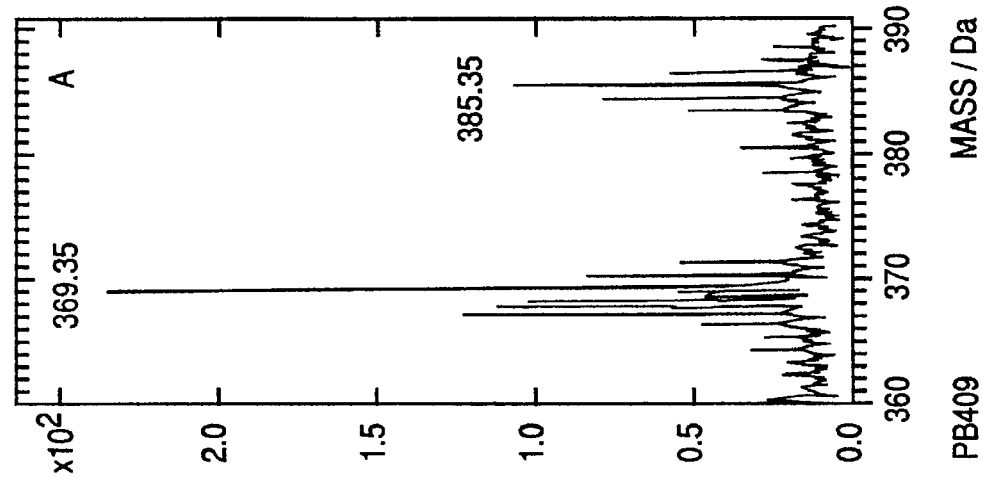

FIG. 1a shows a portion of the TOF-SIMS spectrum for the mass range of 360–390 Da from blood on filter paper from a newborn with normal blood chemistry. The spectrum was obtained directly from the filter paper with no sample pre-treatment. The main peaks of interest for cholesterol are $[M—H]^+$(385.35 Da) and $[M—OH]^+$(369.35 Da). The mass accuracy from spectrum to spectrum was about ±0.03 Da with an approximate mass resolution (M/ΔM)(FWHM) of 3000. The resolution and intensity for cholesterol was better when using a plasma sample collected on filter paper as shown in FIG. 1b. The spectrum of a blank filter paper specimen shows virtually no peaks in this region. FIG. 1c shows a cholesterol standard deposited from solution on filter paper. The pattern obtained from the cholesterol standard closely matches the pattern present in the normal whole blood and plasma specimens.

Figure 2B:
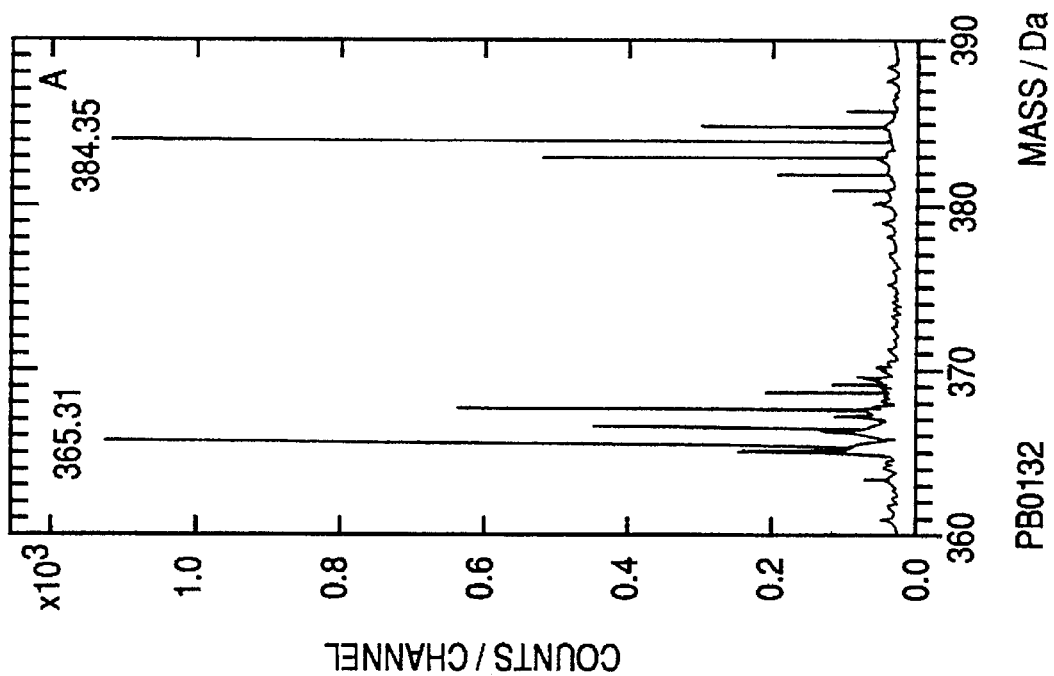
Figure 2A:
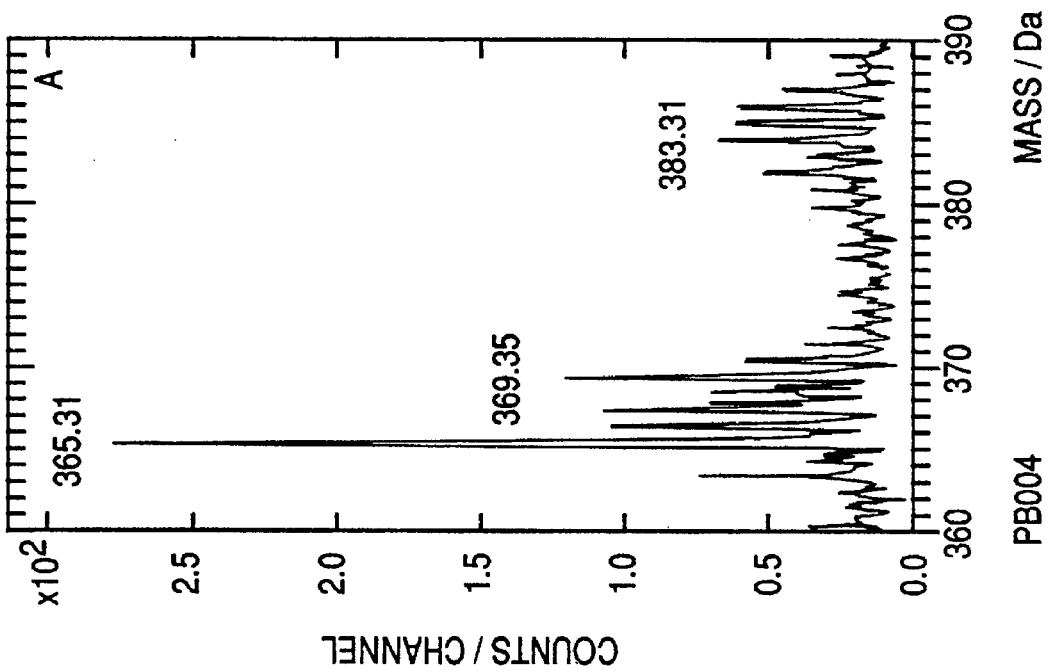

FIG. 2a shows the same portion of a TOF-SIMS spectrum from a filter paper blood specimen from a patient with the SLO syndrome. A large peak was present corresponding to $[M—H_2O—H]^+$(365.31 Da) for 7-dehydrocholesterol, as well as a small cluster of peaks due to $[M—H]^+$(383.32 Da), $[M]^+$(384.33 Da), and $[M+H]^+$(385.34 Da). The intensity of the peak corresponding to $[M—OH]^+$(369.35 Da) for cholesterol was significantly smaller than that seen in a normal specimen. Intuitively, it is expected that $[M—OH]^+$(367.35 Da) should be observed for the 7-dehydrocholesterol, however, an additional loss of $H_2$ is not an uncommon process using an ion beam in SIMS. FIG. 3 shows the likely pathway for double bond formation during the fragmentation of 7-dehydrocholesterol. One cannot tell if the mechanism is concerted or sequential or which position for the double bond is more likely. FIG. 2b shows a TOF-SIMS spectrum of the 7-dehydrocholesterol standard. The $[M]^+$ (384.33 Da) peak is larger than the $[M—H]^+$(383.32 Da) peak in the standard in contrast to the blood sample. This is most likely due to instability of the 7-dehydrocholesterol which will form 7-hydroxycholesterol(402 Da) over time at room temperature, the impurity of the 7-dihydrocholesterol standard and the presence of other isomeric dehydrocholesterols in plasma from SLO patients. The mass spectrum shows a peak corresponding to $[M—H_2O—H]^+$(383.33 Da) from the 7-hydroxy cholesterol.

TABLE

SUMMARY OF SPECIMENS MEASURED
All were measured on dried filter paper whole blood specimens, except for 11–14 which were plasma samples spotted on filter paper.

| Unknown | Intensity Ratio 369.3/365.3 | Patient Age | Diagnosis | Specimen Date | Storage |
|---|---|---|---|---|---|
| 1 | 10.80 ± 0.40 | 30 y | SLO parent | 04/04/94 | −20° C. |
| 2 | 13.10 ± 0.20 | 3 y | SLO phenocopy | 05/12/94 | −20° C. |
| 3 | 0.23 ± 0.01 | 21 y | SLO syndrome | 05/11/94 | −20° C. |
| 4 | 11.80 ± 0.80 | 31 y | SLO parent | 04/05/94 | −20° C. |
| 5 | 1.06 ± 0.05 | 1 d | SLO syndrome | 11/30/94 | R.T. |
| 6 | 12.50 ± 0.80 | 12 y | SLO phenocopy | 11/10/93 | R.T. |
| 7 | 11.20 ± 0.50 | 20 m | Mult. Cong. Anomal. | 09/27/93 | R.T. |
| 8 | 1.26 ± 0.05 | 7 y | SLO syndrome | 01/31/94 | R.T. |
| 9 | 1.60 ± 0.11 | 12 y | SLO syndrome | 01/03/94 | R.T. |
| 10 | 12.10 ± 0.60 | 8 y | SLO phenocopy | 10/04/93 | R.T. |
| 11 | 18.00 ± 1.40 | — | Normal plasma | — | −20° C. |
| 12 | 18.20 ± 1.40 | — | Normal plasma | — | −20° C. |
| 13 | 10.80 ± 0.10 | — | Normal plasma | — | −20° C. |
| 14 | 14.20 ± 0.50 | — | Normal plasma | — | −20° C. |
| 15 | 0.38 ± 0.06 | 2.5 y | SLO syndrome | 01/28/94 | R.T. |
| 16 | 12.90 ± 0.40 | 2 d | Normal newborn | — | R.T. |
| 17 | 11.20 ± 0.70 | 2 d | Normal newborn | — | R.T. |
| 18 | 14.10 ± 1.10 | 2 d | Normal newborn | — | R.T. |
| 19 | 15.30 ± 1.20 | 2 d | Normal newborn | 11/28/89 | R.T. |
| 20 | 1.60 ± 0.19 | 2 d | SLO syndrome | 11/28/89 | R.T. |
| 21 | 15.00 ± 1.20 | 2 d | Normal newborn | 11/28/89 | R.T. |
| 22 | 14.00 ± 0.70 | 2 d | Normal newborn | — | R.T. |
| 23 | 3.40 ± 0.90 | 2 d | SLO syndrome | — | R.T. |
| 24 | 17.10 ± 1.50 | 2 d | Normal newborn | — | R.T. |
| 25 | 0.29 ± 0.02 | — | SLO syndrome | — | −20° C. |
| 26 | 0.31 ± 0.04 | — | SLO syndrome | — | −20° C. |
| 27 | 1.80 ± 0.04 | 4 d | SLO syndrome | 01/20/92 | R.T. |
| 28 | 1.64 ± 0.11 | 2 d | SLO syndrome | 11/27/93 | R.T. |

Figure 4B:
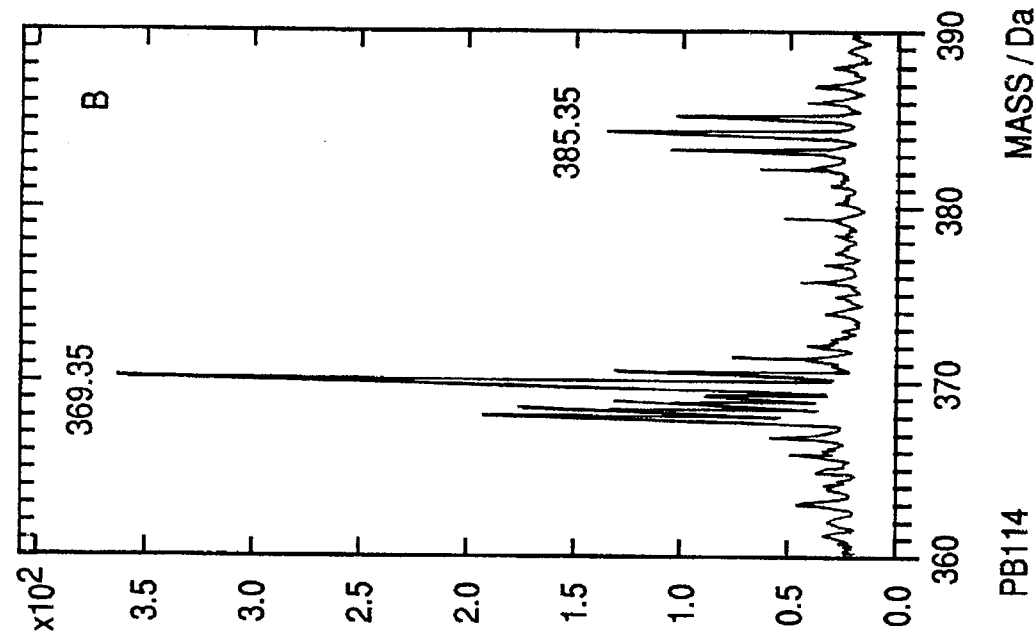
Figure 4A:
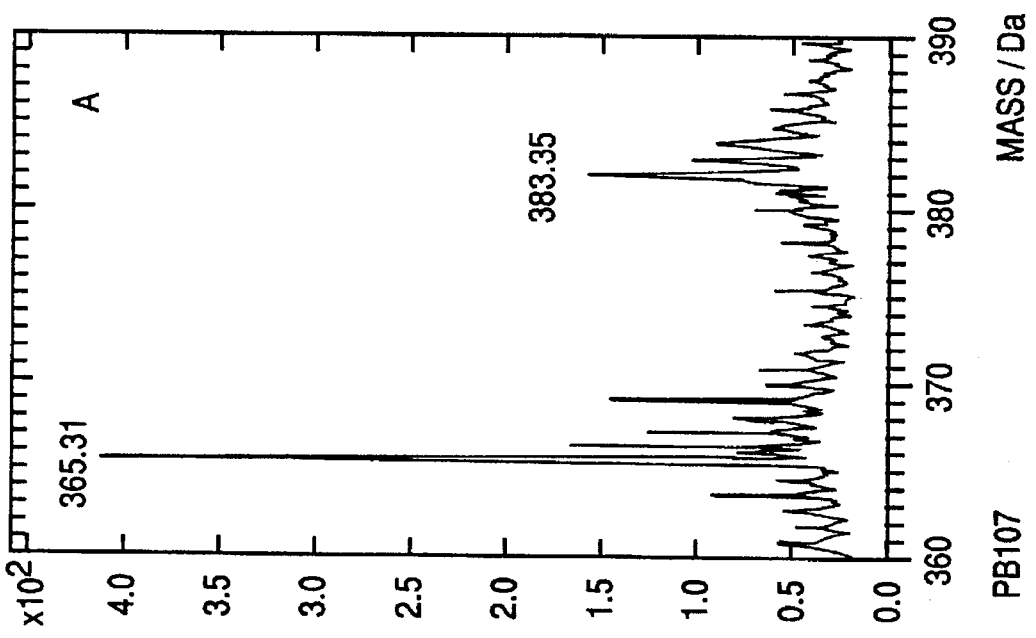

Twenty-eight blinded unknown specimens were obtained from normal individuals and individuals with the SLO syndrome, as seen in the table hereinabove. These were analyzed using TOF-SIMS and each sample was identified correctly with no false-positives or false-negatives. FIGS. 4a and 4b show two spectra from the unknown set. Table 1 summarizes the ratio of the 369.35 Da peak (cholesterol) to the 365.31 Da peak (7-dehydrocholesterol) for the 28 samples analyzed. The ratios that are ≧10.0 are from individuals which are not affected with the SLO syndrome. Cases 1, 2, 4, 6, 7, 10–14, 16–19, 21, 22 and 24 were from normal samples. Samples 3, 25 and 26 were from patients with typical severe SLO syndrome. Patients ranged in age from new born to 21 years of age. All four of these specimens were stored at −20° C. Samples 5, 8, 9, 20, 27 and 28 are from newborns with SLO syndrome and were stored at room temperature for up to five years. Sample 23 was from a patient with clinically and biochemically milder forms of the SLO syndrome. Additionally, the Table gives the patient's age, time of sample collection and mode of sample storage. It, therefore, appears that specimens from the clinically and biochemically abnormal cases have cholesterol/7-dehydrocholesterol ratios <0.5 (369.3/365.3 intensity ratios), provided they are tested fresh or stored frozen. If stored for some time at room temperature or if from milder forms of the SLO syndrome, the ratios are 1.06 to 3.40, which is still clearly abnormal. This is consistent with the degradation of 7-dehydrocholesterol when stored at room temperature. Despite the sample storage conditions, clear visual distinctions can be made between the two spectra using the $[M—H_2O—H]^+$ (365.31 Da) peak which is present with a high intensity in SLO patients and is nearly absent in normal individuals.

Whereas particular embodiments of the invention have been described herein for purposes of illustration, it will be evident to those skilled in the art that numerous variations of the details may be made without departing from the invention as set forth in the appended claims.

What is claimed is:

1. A method of of analyzing cholesterol containing organic samples for Smith-Lemli-Opitz Syndrome using, Time-of-Flight Secondary Ion Mass Spectrometry (TOF-SIMS) without derivation and chemical steps, comprising the steps of:

a. vaporizing said sample to convert it into a vaporized sample;
   b. ionizing said vaporized sample;
   c. detecting fragment ions of said vaporized, ionized sample;
   d. determining a ratio of said fragment ions for cholesterol/7-dehydrocholesterol in said sample: and
   e. determining whether said Smith-Lemli-Opitz Syndrome is present by comparing said ratios of fragment ions for cholesterol/7-dehydrocholesterol in said sample with ratios that define Smith-Lemli-Opitz Syndrome.

2. The method of claim 1, employing kiloelectronvolt ion beams as a means to effect both said vaporizing and ionizing steps.

3. The method of claim 1, employing blood plasma as said organic sample.

4. The method of claim 1, employing as said organic sample at least one material selected from the group consisting of blood cells and blood tissue.

5. The method of claim 1, employing serum as said organic sample.

6. The method of claim 1, including determining that Smith-Lemli-Opitz Syndrome is present in severe form if the peak ratio of cholesterol/7-dehydrocholesterol is less than 0.5.

7. The method of claim 1, employing said organic sample spotted on filter paper.

8. The method of claim 1, including determining that SLO is present if the ratio is cholesterol/7-dehydrocholesterol peaks is less than about 3.5.

9. The method of claim 1, including determining that Smith-Lemli-Opitz Syndrome is present if the peak ratio of cholesterol/7-dehydrocholesterol is less than about 3.5.

* * * * *